United States Patent
Jones et al.

(10) Patent No.: US 9,272,251 B2
(45) Date of Patent: Mar. 1, 2016

(54) METHOD AND APPARATUS FOR MAINTAINING MICROCARRIER BEADS IN SUSPENSION

(75) Inventors: Christopher Jones, Cardiff (GB); Philip John Meyler, Cardiff (GB); Rhys Evans, Cardiff (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 681 days.

(21) Appl. No.: 13/266,554

(22) PCT Filed: Apr. 23, 2010

(86) PCT No.: PCT/EP2010/055477
§ 371 (c)(1),
(2), (4) Date: Oct. 27, 2011

(87) PCT Pub. No.: WO2010/125006
PCT Pub. Date: Nov. 4, 2010

(65) Prior Publication Data
US 2012/0045834 A1    Feb. 23, 2012

(30) Foreign Application Priority Data
Apr. 28, 2009 (GB) .................................. 0907260.4

(51) Int. Cl.
| | |
|---|---|
| *B01F 7/22* | (2006.01) |
| *B01F 7/18* | (2006.01) |
| *B01F 7/00* | (2006.01) |
| *C12M 1/06* | (2006.01) |
| *C12M 1/00* | (2006.01) |

(52) U.S. Cl.
CPC ............... *B01F 7/18* (2013.01); *B01F 7/00275* (2013.01); *B01F 7/22* (2013.01); *C12M 27/02* (2013.01); *C12M 29/04* (2013.01); *C12M 47/12* (2013.01)

(58) Field of Classification Search
CPC ................ B01F 7/06; B01F 7/20; B01F 7/22; B01F 7/00366; B01F 7/00375; B01F 7/00341; B01F 7/00275; B01F 7/00383
USPC ....................... 366/65, 66, 270, 330.1–330.7, 366/325.92–325.93; 416/237; 422/224–228; 261/84, 91
See application file for complete search history.

(56) References Cited

U.S. PATENT DOCUMENTS

| | | |
|---|---|---|
| 4,355,906 A | 10/1982 | Ono |
| 4,382,685 A | 5/1983 | Pearson |
| 4,512,666 A | 4/1985 | O'Connell |
| 4,634,675 A | 1/1987 | Freedman et al. |
| 5,267,791 A | 12/1993 | Christian et al. |
| 5,277,550 A | 1/1994 | Kato et al. |
| 5,297,938 A | 3/1994 | Von Essen et al. |

(Continued)

FOREIGN PATENT DOCUMENTS

| | | |
|---|---|---|
| EP | 0 254 494 | 9/1992 |
| JP | 61 074574 | 4/1986 |

(Continued)

*Primary Examiner* — Charles Cooley
(74) *Attorney, Agent, or Firm* — Sutherland Asbill & Brennan LLP

(57) ABSTRACT

The invention relates to an impeller for use in a bioreactor for growing adherent mammalian cells and/or a cell separator for adherent mammalian cells. The impeller of the invention is designed to efficiently and rapidly lift a bed of settled cells and microcarrier beads at low rotational speeds. Cell growth and concomitant yield is therefore improved by maintaining the culture in an environment of low shear force.

14 Claims, 10 Drawing Sheets

(56) References Cited

U.S. PATENT DOCUMENTS

| | | | |
|---|---|---|---|
| 5,316,443 A | 5/1994 | Smith | |
| 6,334,704 B2* | 1/2002 | Noda et al. | 366/262 |
| 7,296,925 B2* | 11/2007 | Himmelsbach et al. | 366/330.3 |
| 9,108,170 B2* | 8/2015 | Wang | B01F 7/00275 |
| 2004/0174769 A1 | 9/2004 | Weetman | |
| 2004/0228210 A1* | 11/2004 | Himmelsbach et al. | 366/330.3 |
| 2005/0007874 A1* | 1/2005 | Roszczenko et al. | 366/270 |
| 2006/0187750 A1* | 8/2006 | Aldrich et al. | 366/270 |
| 2007/0139442 A1* | 6/2007 | Robinson | 345/629 |
| 2008/0130406 A1* | 6/2008 | Rosso et al. | 366/342 |
| 2012/0045834 A1* | 2/2012 | Jones et al. | 435/383 |
| 2015/0044057 A1* | 2/2015 | Dinnison | |
| 2015/0165399 A1* | 6/2015 | Rawlings | |

FOREIGN PATENT DOCUMENTS

| | | |
|---|---|---|
| RU | SU 1114696 | 9/1984 |
| WO | WO 2011122370 A1 * | 10/2011 |

* cited by examiner

METHOD AND APPARATUS FOR MAINTAINING MICROCARRIER BEADS IN SUSPENSION

CROSS-REFERENCE TO RELATED APPLICATIONS

This application is a filing under 35 U.S.C. §371 and claims priority to international patent application number PCT/EP2010/055477 filed Apr. 23, 2010, published on Nov. 4, 2010 as WO 2010/125006, which claims priority to application number 0907260.4 filed in Great Britain on Apr. 28, 2009.

FIELD OF THE INVENTION

The present invention relates to the fields of biotechnology, especially the field of tissue culture. In particular, the invention relates to an impeller for stirring microcarrier beads within a liquid culture suspension to enable the growth and processing of anchorage-dependent or adherent mammalian cells.

BACKGROUND TO THE INVENTION

The development of High Throughput Screening (HTS) assay procedures for the identification of potential drug candidates has established the need for large numbers of cells for each type of test. As a consequence there is a significant challenge to overcome the "culturing burden" to enable multiple billions of cells to be grown for each screen. Anchorage-dependent or adherent cells are of particular interest to the drug industry as many different cells, including most cells derived from solid tissues, require a surface to grow and differentiate. The use of support particles or microcarrier beads (e.g. CYTODEX™ particles (GE Healthcare)) in cell culture methods has improved the yields of adherent cells by increasing the surface area for growth. A range of microcarrier beads are available including dextran (e.g. CYTODEX™) and polystyrene beads coated with a variety of polymers (e.g. gelatine, collagen, FACT, ProNectin F; Sigma-Aldrich).

Microcarrier beads for cell culture provide a large surface area for growing adherent cells to very high cell densities. Maximum cell densities are dependant on the efficient seeding of cells onto the microcarriers. Typically at least 80% of beads should be coated with 5 to 15 cells per bead at the start of the culture phase. To attain this criterion requires a controlled cell seeding phase in which cells and beads are in an environment having both static and dynamic phases. The cells and microcarrier beads settle at different rates: the beads being denser than cells settle before them. The microcarriers will settle to form a bed at the bottom of the culture vessel, the depth of the bed being dependent upon the number of microcarrier beads present. As cells begin to settle, the beads located near the top of the bed will be most likely to receive cells. The cells will begin to attach within minutes, typically within 5 to 60 minutes. However, if the environment were to remain static, non-uniform coating of microcarriers would occur, the microcarriers at the top of the bed being coated with many more cells than beads located within or at the bottom of the bed volume which may receive very few or even no cells. It is therefore necessary to turn over or agitate the microcarrier bed in order to expose the surface area of all the beads to the available cells. Since adherent cells are generally only loosely attached to microcarrier beads at the early stage of seeding, great care must be taken to minimise excessive shear forces which could result in cell detachment and/or cell injury. This can be a problem if a significant bed volume of microcarrier beads has to be turned over.

The problem of maintaining microcarrier beads in liquid suspension whilst minimising shear forces has been addressed previously. For example, U.S. Pat. No. 4,382,685 (Pearson) describes an apparatus for stirring particles in a liquid medium. The stirrer is a rod with a bulbous tip which describes an orbital path in the vessel to sweep out an annular trough or channel formed in the bottom of the vessel. The apparatus is designed for stirring microcarriers in a liquid culture medium to maintain them in uniform suspension at low stirring speeds to avoid damage to growing cells. U.S. Pat. No. 4,355,906 (Ono) describes an apparatus which includes a rotatable stirrer for maintaining microcarrier beads in suspension in cell culture. The stirrer assembly includes at least one blade radially disposed with respect to the vessel axis and is connected to the assembly adjacent a magnet for rotation about the axis. U.S. Pat. No. 4,512,666 (O'Connell) relates to suspended magnetic stirrers, in particular, a suspended magnetic impeller the height of which can be adjusted by means of a movable bearing. See also U.S. Pat. No. 5,267,791 (Christian et al); U.S. Pat. No. 4,634,675 (Freedman et al).

EP 254494 B1 (Davidson et al.) provides a description of known impellers in use for stirring liquids. These include impellers known as the "disk turbine" or "Rushton" impeller in which each paddle of the impeller generally consists of a rectangular-shaped sheet which is mounted around the periphery of a disc or spindle. Other forms of known impeller include the standard "marine" impeller having up to three or four curved blades fixed around a central spindle; and the pitched blade impeller having strip-like blades extending radially outwards from a spindle, each of which is mounted at an angle to the axis of the of the shaft. In operation, liquid is propelled away from the impeller in parallel to the axis of the shaft thereby generating circulation loops within the vessel. Furthermore, standard impellers, such as marine, Rushton or pitched blade are incapable of lifting beads into suspension without the use of high rotational speeds, typically in excess of 60 rpm (revolutions per minute). As a consequence of the high rotational speed and extended time required to lift a large bed volume of microcarriers beads, cells can be damaged and loss of adhesion between cells and microcarrier beads can occur due to excessive shear forces.

JP61074564 (Toyo Boseki) describes an impeller which can be used for the uniform agitation of cells even at low rotational speed and to facilitate the separation of cells from microcarriers after the completion of culture growth. The impeller comprises alternating flat and curved blades, the flat blade forming a radial flow perpendicular to the rotary shaft, and the curved blade forming an axial flow parallel to the rotary shaft.

US 2004/0174769 (Weetman) discloses impellers which are adapted for use in surface aeration of liquids in a tank when disposed on the surface of the liquid in the tank. The aeration efficiency of the impeller is improved by curving the top portions of its and providing an opening or a slot on the blades through which a portion of the liquid may pass.

U.S. Pat. No. 5,277,550 (Kato et al.) relates to agitating vanes for use in a device for agitating and mixing liquid or gases in food processing and the chemical industries. The vanes are designed to produce efficient agitation without damaging microorganisms by reducing eddy flows and peeled-off eddy flows. This effect is achieved by mounting several curved or auxiliary vanes at right angles to a flat vane in a spaced-apart relationship. While such vanes or impellers may be employed for agitating microorganisms, they would not be suitable for use with more sensitive cells such as mammalian cells.

U.S. Pat. No. 5,316,443 (Smith) discloses liquid mixing impellers particularly designed for the chemical processing industry which provide a generally axial flow when rotated in a first direction and a generally radial flow when rotated in the opposite direction. The blades have at their leading edges a curved and folded back section of relatively short chordwise extent, so as to form a concave pocket immediately behind the leading edge.

U.S. Pat. No. 5,297,938 (Von Essen et al.) relates to hydrofoil impellers for use in mixing apparatus which have a high efficiency liquid pumping action and enhanced power stability. The hydrofoil impellers disclosed in the document would not be suitable for use in a bioreactor or cell separator because this pumping action would injure the cells.

SU1114696 (Karpovich et al.) discloses a microorganism cultivating apparatus for hydrogen acid forming bacteria. Two flat bladed mixers agitate the gas-liquid mixture and separate, discrete vertical plates having curved ends are used to disperse the mixture and organise its movement through the circulation contour.

Thus, although the importance of achieving suitable agitation in an environment of low shear force has been recognised, it has been found that none of the impellers described in the prior art provide a solution to this problem. Indeed, none of the prior art documents described above offer a means to completely overcome the requirement to efficiently lift cells and microcarrier beads in a manner that turns over the entire population of cells and/or beads in an environment of low shear force, thereby minimising cellular injury and ensuring that low affinity interactions between cells and beads is retained. The present invention addresses this need by the provision of an impeller device that efficiently and rapidly lifts a bed of settled cells and microcarrier beads at low rotational speeds. Cell growth and concomitant yield is therefore improved by maintaining the culture in an environment of low shear force.

Another problem encountered in the large scale production of adherent cells which are grown on microcarrier beads is that of separating the cells from the beads at the end of the process. The cells are often treated with enzyme solutions, such as trypsin, at the end of the process to facilitate separation from the beads. However, enzymic means are seldom sufficient on their own to effect this separation, and some form of physical agitation is also required to increase yields of the cells. Care must be taken in applying this agitation otherwise the cells will be injured in the process. In one aspect, the present invention addresses this problem by the use of an impeller which can agitate cells at low rotational speeds.

SUMMARY OF THE INVENTION

According to a first aspect of the present invention, there is provided an impeller (10) for use in a bioreactor for adherent mammalian cells and/or a cell separator for adherent mammalian cells comprising: a hub (20) for attachment to a rotatable shaft (25), one or more blades (30) attached to the hub (20), each blade comprising a first side (31) adjacent to the hub (20), a second side (32) and a third side (33) adjacent to and at right angles to the first side (31); a fourth side (34) opposed to the first side (31) and forming an outer edge of the blade; and a surface (35) having a planar portion (36) and a curved portion (37); wherein the curved portion is angled in the range of 70 to 120° to the plane of said planar portion (36) to form a leading surface relative to the direction of rotation of the impeller: wherein the fourth side outer edge includes a generally straight portion merging into said curved portion as seen in FIGS. 1, 8, and 9. The second and third sides define a height therebetween and the outer edge is disposed at a length from said hub whereby the length is greater than the height as seen in FIGS. 2 and 3.

A bioreactor is a vessel which has been designed for carrying out a process involving cells or biochemically active substances obtained from those cells.

Bioreactors are usually cylindrical in shape, typically ranging from one liter to several hundred liters in capacity. They are usually made of glass or stainless steel, so that they are chemically and biologically inert and allowing them to be sterilised (e.g. by autoclaving). Their design can be complex to maintain optimum growth conditions such as dissolved oxygen levels (using gases such as air, oxygen, nitrogen), pH (using carbon dioxide and sodium bicarbonate) and temperature control. A key element is the agitation which allows cells to be maintained in suspension without suffering damage through agitation and/or physical abrasion.

A cell separator is a device which is used to separate a mixture of cells and beads, thus allowing the cells to be harvested.

In one aspect, the curved portion (37) is angled in the range of 80 to 100° to the plane of the curved portion (36). Preferably, the curved portion (37) is angled at 90° to the plane of the planar portion (36).

In another aspect, the second side (32) is shorter than the third side (33).

Preferably, the curved portion (37) constitutes 20 to 40% of the area of said surface (35). More preferably, the curved portion (37) constitutes 30% of the area of the surface (35).

In a further aspect, the curved portion (37) is curved upwards to enhance the agitation and mixing of the growth medium.

In one aspect, each blade (30) is reversibly attached to the hub (20). This allows the user to replace damaged or worn blades, or to change the size of blades for bioreactors or cell separators of different volumes.

In another aspect, each blade (30) is irreversibly attached to the hub (20) to facilitate ease and cost of production.

The impeller is used for maintaining microcarrier beads comprising adherent mammalian cells in suspension in a bioreactor. In one aspect, the adherent cells are human cells. In another aspect, the adherent cells are stem cells or cells derived from stem cells.

Preferably, the hub (20) and/or the blade (30) is made of a sterilisable inert material.

In one embodiment, the impeller comprises four blades (30).

In a second aspect of the present invention, there is provided a method for growing adherent mammalian cells, the method comprising:
a) adding adherent mammalian cells to growth medium in a bioreactor;
b) stirring the growth medium with the impeller as hereinbefore described;
wherein the impeller is rotated at a speed of 10 to 55 rpm. The use of such low rotational speeds maintains the cells and suspension without causing any injury to the cells. In one aspect, the cells are human cells. In another aspect, the cells are stem cells or cells derived from stem cells.

In one aspect, the cells are attached to microcarrier beads prior to adding the cells to the growth medium in the bioreactor.

In another aspect, the growth medium contains microcarrier beads and the cells attach to the beads while the impeller is stirring the growth medium. This obviates the need to seed microcarrier beads with cells prior to addition to the growth medium and thus saves user time and simplifies the work flow.

Preferably, the impeller is rotated at a speed of 15 to 30 rpm. More preferably, the impeller is rotated at a speed of 25 rpm.

In a third aspect of the present invention, there is provided a use of an impeller as hereinbefore described for growing cells in a bioreactor, characterised in that the impeller is rotated at a speed of 10 to 55 rpm. In one aspect, the adherent cells are human cells. In another aspect, the cells are stem cells.

According to a fourth aspect of the present invention, there is provided a bioreactor or a cell separator comprising an impeller (10) as hereinbefore described.

In one aspect the bioreactor or cell separator comprises a head plate (42), a cylindrical wall (46), a base (44) and attachment means for securing the cylindrical wall to the head plate and the base.

The cell separator may further comprise:
a cylindrical sieve (80) attached to the head plate (42) and enclosing the impeller (10) to form an inner chamber (82) for separating cells from microcarrier beads within and an outer chamber (84) for collecting cells therefrom;
an inlet (47) for feeding cells and microcarrier beads into the inner chamber (82); and
an outlet (48) for collecting cells from the outer chamber; wherein the sieve comprises a first mesh having a plurality of pores of a size that permits the flow of cells through to the outer chamber but excludes the passage of microcarrier beads.

In another aspect, the sieve additionally comprises a second mesh having a plurality of pores of a size greater than that of the pores of the first mesh. The second mesh thus acts to support the first mesh.

In a further aspect, the cell separator additionally comprises a sparger attached to the inlet.

DETAILED DESCRIPTION OF THE INVENTION

Figure 1:
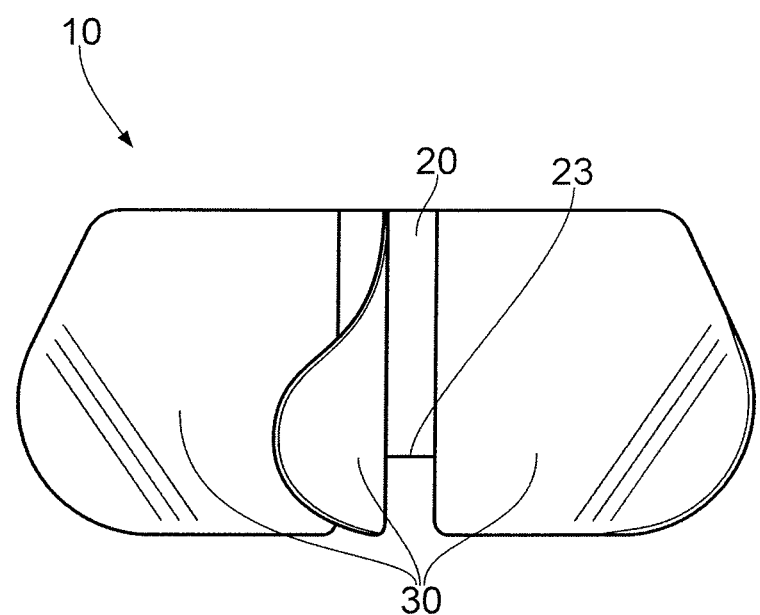
FIG. 1 is a side view of the impeller according to one embodiment of the invention.
Figure 2:
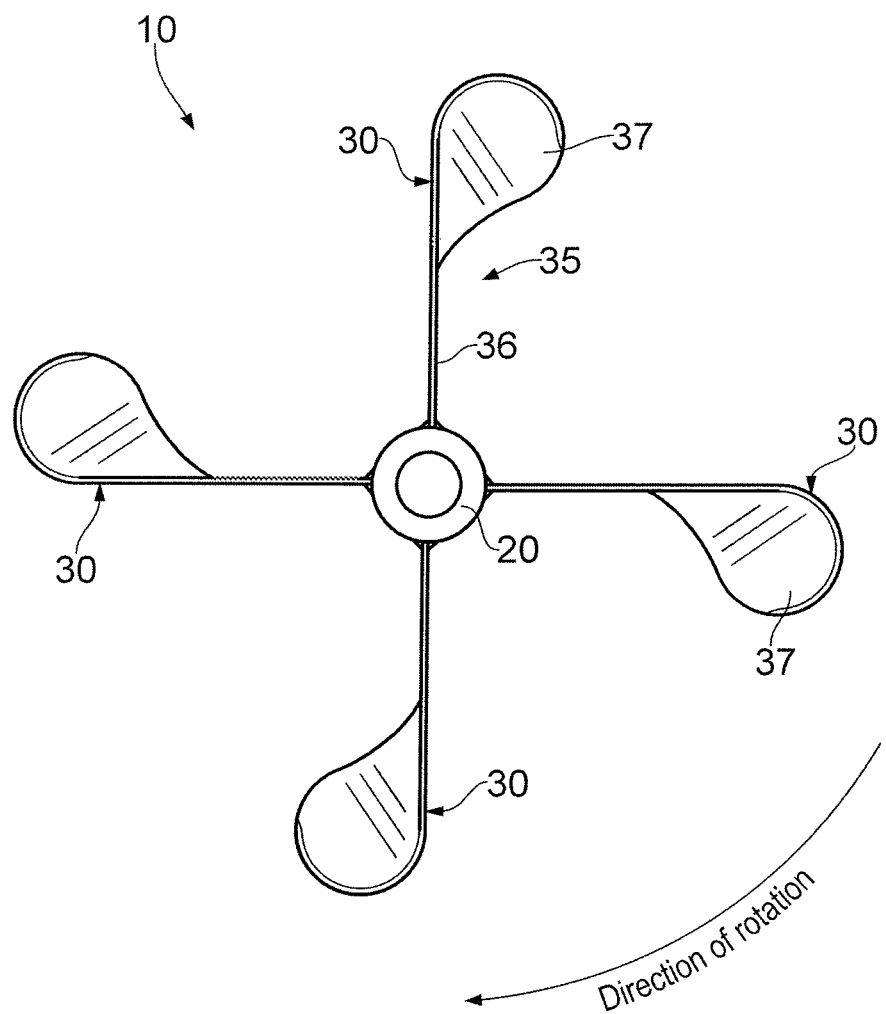
FIG. 2 is a view in plan of the impeller according to one embodiment of the invention.
Figure 3:
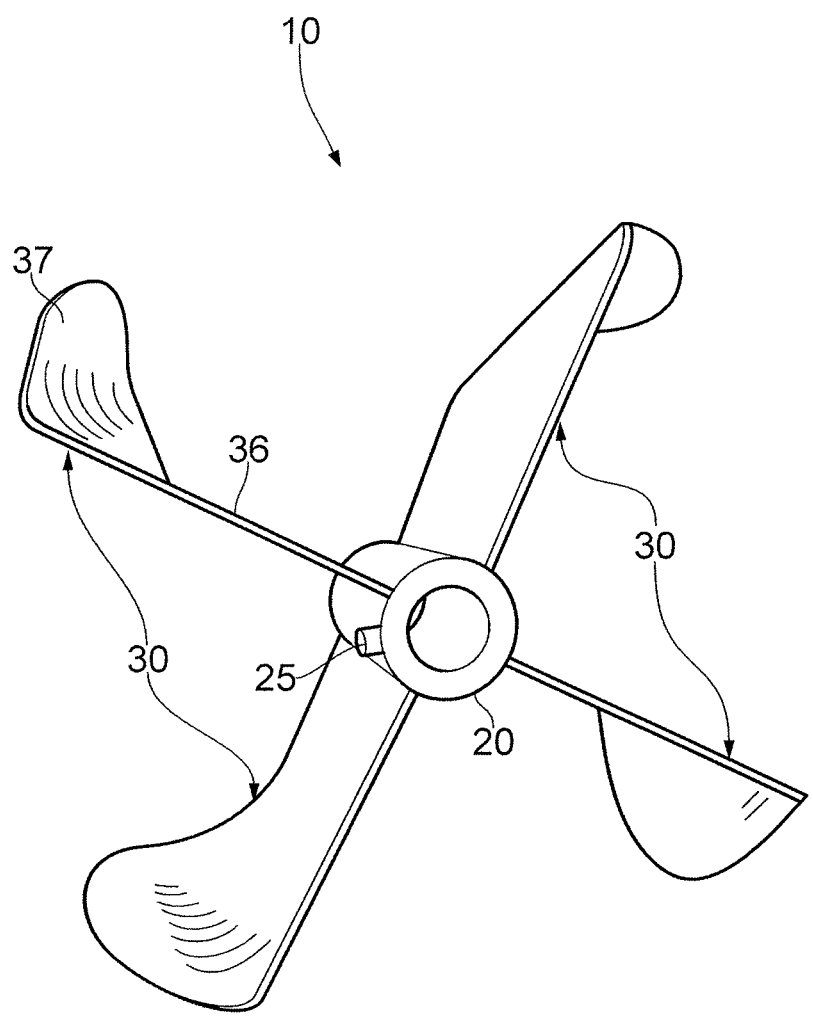
FIG. 3 is a plan view in perspective of the impeller according to one embodiment of the invention.

Referring now to FIGS. 1, 2 and 3, there is shown an embodiment of the impeller (10) in side view, in plan view, and in plan perspective, respectively. The impeller includes four blades (30) (three being shown in FIG. 1, the fourth extending into the plane of the paper) each impeller blade being mounted onto a hub (20) which is rotatable on a shaft (not shown) which, in turn is rotated by suitable means, for example an electric motor (not shown). In this embodiment, each of the impeller blades (30) are radially disposed around the circumference of the hub (20) at 90° intervals from each other.

In one embodiment (as shown in FIG. 1), each impeller blade (30) may extend to the same extent and a little below the end portion (23) of the impeller hub (20). In another embodiment, the lower end of the impeller hub (23) is in line with the lower edge of each blade.

In one embodiment, the shaft is dimensioned to be a friction fit inside the hub (20) of the impeller (10) and may be fixed in place by suitable means such as welding or by the use of appropriate adhesives.

In another embodiment, the hub (20) of the impeller (10) is detachable from the shaft so as to facilitate removal of the impeller and replacement with another impeller having different overall dimensions and/or numbers of blades. In this embodiment the hub (20) is provided with one or more threaded holes for receiving tensioning means (25) such as a grub screw for tightening the hub onto the shaft of the impeller (FIG. 3).

Figure 4:
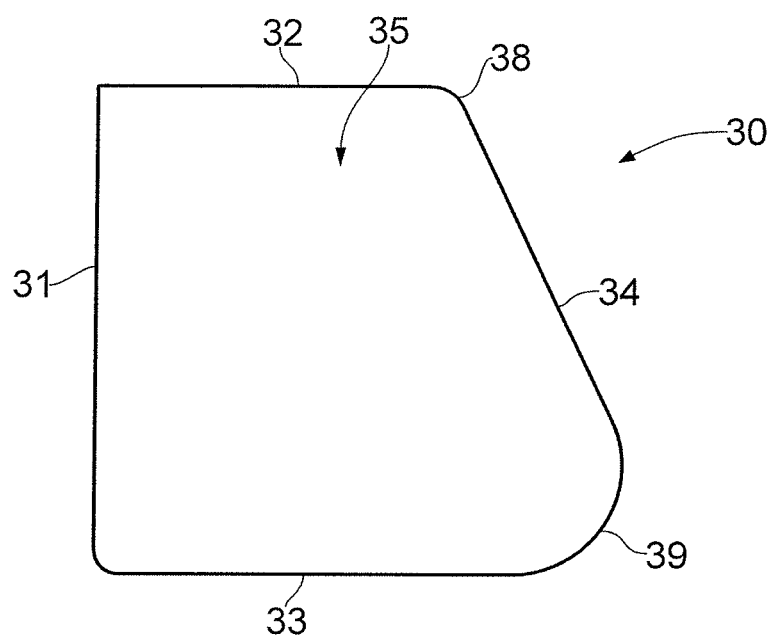
FIG. 4 is a side view of a solid sheet in the form of a right angled trapezium having two rounded corners (38) and (39) for formation of an impeller blade according to the invention.
Figure 5:
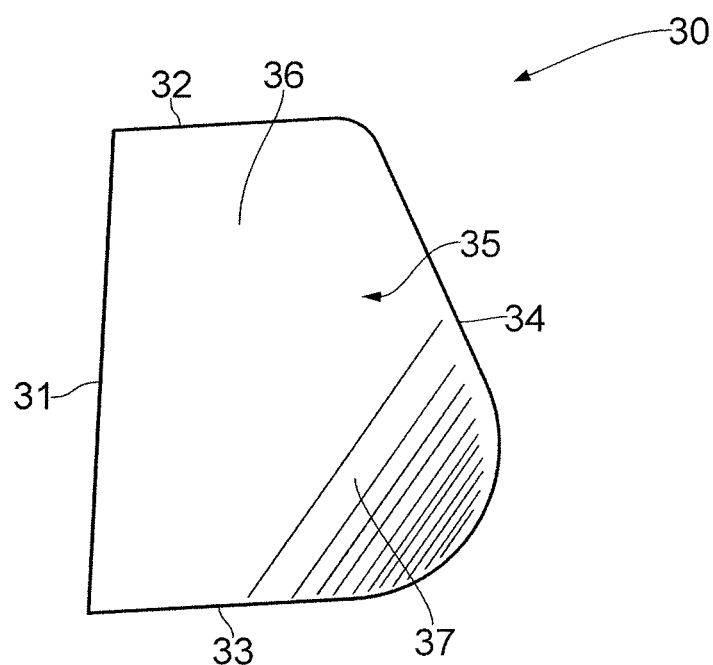
FIG. 5 is a side view of an impeller blade according to an embodiment of the invention.

Each of the blades of the impeller (10) is identical in both shape and orientation. As shown in FIGS. 4 and 5, the corners of the leading edge of the blade (that is, the edge nearest to the walls of a vessel or bioreactor into which the impeller is mounted) may have a rounded profile (38, 39).

Each blade (30) of the impeller is formed from a substantially flat solid material having first (31), second (32), third (33) and fourth (34) sides and wherein the first (31) side is attached longitudinally to the hub (20); the second and third sides being substantially parallel one with the other; and the fourth side constituting the blade tip. The blades are arranged in relation to the impeller hub such that, when the impeller is viewed with its axis of rotation vertical and in plan, the leading surface of each of the blades has a rounded profile, curved upwards and in the direction of rotation of the impeller.

The impeller is made of a material which is chemically and biologically inert. Suitable examples include metal, glass, ceramic, carbon fibre, fibre glass and plastics such as PTFE, nylon and PERSPEX®). Typical metals include high quality stainless steel, such as grade 316 which has superior corrosion resistance properties. The blades can be manufactured by a number of different processes, depending upon the nature of the material used. In one embodiment, the blades are manufactured from high quality stainless steel (e.g. grade 316 stainless steel) and are cut or press-stamped from a single sheet having a constant thickness of approximately 1 to 2 mm to form a right-angled trapezoid shape (FIG. 4). One portion of the surface (35) is then bent, using standard procedures well known in the art (e.g. using a conventional jig) to divide the blade into a planar portion (36) and a curved portion (37) which is angled at a 70 to 120° relative to each other, such that the curved portion (37) extends outwards and upwards from the plane of the planar portion (36), as depicted in FIG. 5.

Other suitable materials including plastic (e.g. nylon, PTFE, PERSPEX®), glass (e.g. ceramics), carbon fibre and fibre glass can be used to manufacture the impeller blades of the invention. Suitable techniques for fabricating plastic blades include injection moulding to produce blades of 2-3 mm thickness. Glass blades can be manufactured by standard techniques well known to the skilled person.

For a 7.5 L bioreactor, such as the New Brunswick BioFlo 110 bioreactor, typical blade dimensions are a blade height (i.e. first side 31) of approximately 67 mm, a first width (second side 32) of 45 mm and second width (i.e. third side 33) of 65 mm.

The central hub (20) of the impeller (10) may take the form of a barrel (as shown in FIG. 1), collar or bush through which a drive shaft (not shown) can be inserted for rotation of the impeller, the axis of rotation of the impeller being defined by the drive shaft. One or more fasteners may be employed in order to secure the hub of the impeller to the drive shaft. As an example, a grub screw may be received through a threaded aperture (25) in the hub which can be tightened against the drive shaft in a conventional manner. In other embodiments, the hub can be provided with other fastening means (e.g. split pins, bolts, and the like).

In another embodiment, each said blade (30) is detachably mounted onto the hub (20) via suitable attachment means. This embodiment thereby enables the attachment or removal of one or more of the blades from the hub depending on the specific requirements of the operator and the properties of the microcarriers to be stirred. According to this embodiment, each extending impeller blade (30) is frictionally held between the walls of a channel or groove formed in the hub (20). The hub may therefore contain one, two, three or four such grooves, thereby allowing up to four such impeller blades to be fitted to the hub.

Figure 6:
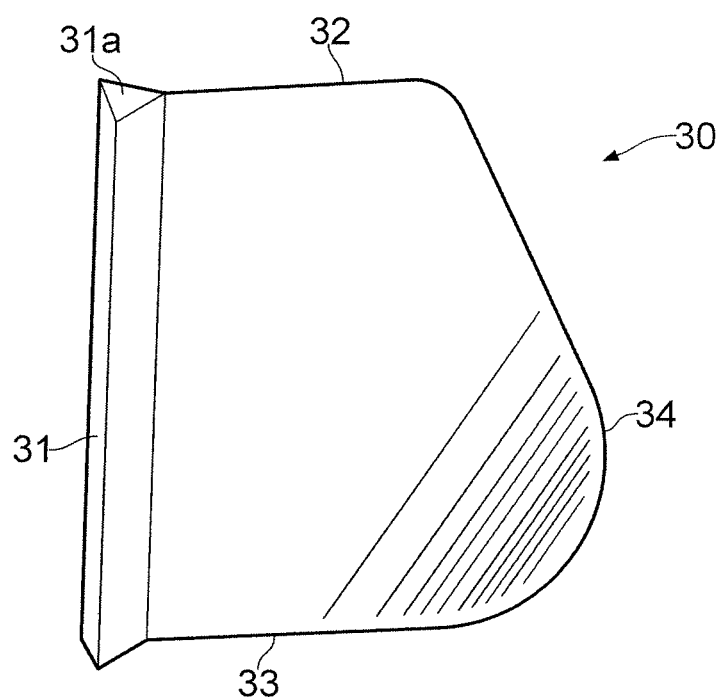
FIG. 6 is a view in perspective of an impeller blade according to an alternative embodiment of the invention.

In this embodiment, the inner edge or side (31) of the, or each detachable impeller blade in contact with the hub, is shaped throughout its length so as to be a friction fit within the walls of a groove provided longitudinally in the hub. The cross-sectional shape of this inner edge or side (31) may be circular, square or triangular. Attachment of the impeller blade (30) to the hub (20) is accomplished by means of a sliding motion of the blade within and along the channel, so that the impeller blade is held in registry with the hub. In a preferred embodiment, the inner edge of each such detachable blade (30) is of a triangular cross-section (31a) radiating outwards from the plane of the blade (FIG. 6). Such a cross-sectional shape of the inner edge results in minimal sideways movement of the impeller blade relative to the hub, thereby allowing optimum stirring efficiency.

Figure 7A:
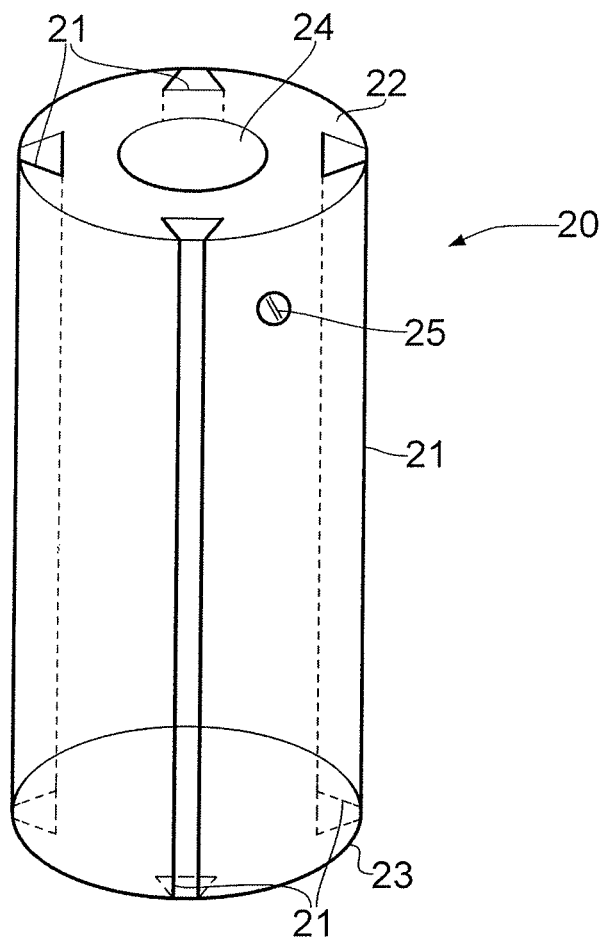
FIG. 7 is a view in perspective (7A) and in plan (7B) of the hub of the impeller according to one embodiment of the invention.
Figure 7B:
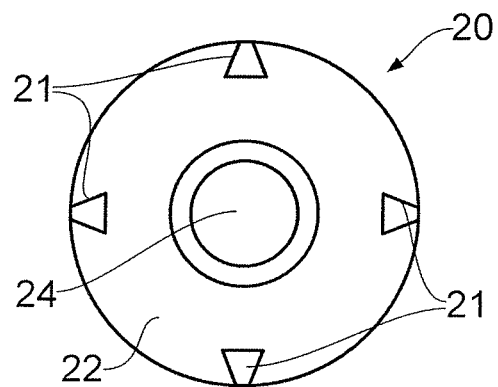

FIG. 7A depicts a hub (20), with an upper (22) and lower (23) end and having a central bore (24) for attachment to a drive shaft (not shown). The hub (20) has a series of triangular grooves (21) running along its longitudinal axis for attachment to a blade having a triangular end piece or side (31) shown in FIG. 6 (31). The hub (20) is shown in plan view in FIG. 7B, highlighting the central bore (24) and triangular grooves (21). It will be understood that the number of grooves (21) may vary to accommodate, for example, 1, 2, 3, 4, 5, 6, 7, 8, 9, 10, 11 or 12 blades and is not limited to the four shown in the diagram.

Figure 8:
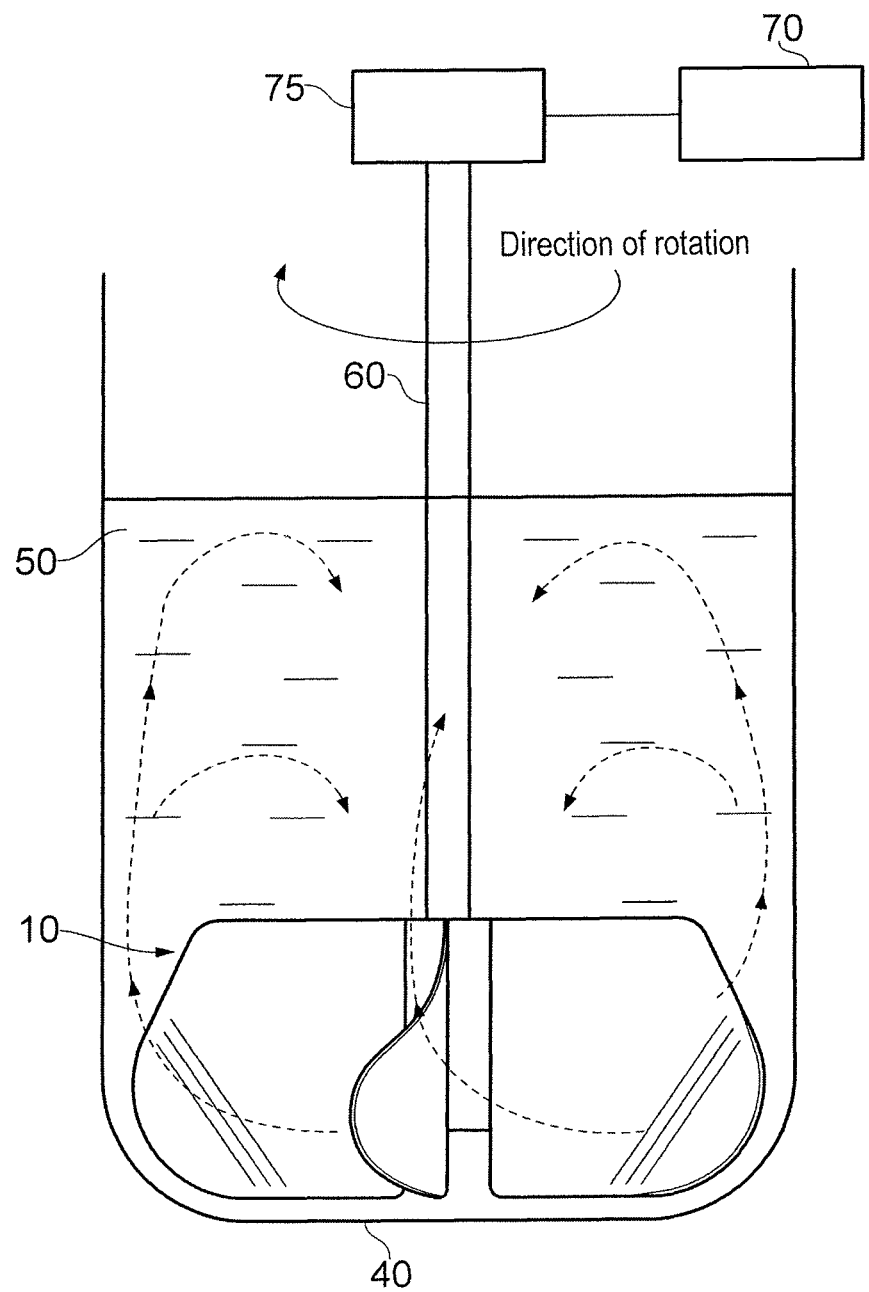
FIG. 8 is a schematic representation of a bioreactor incorporating an impeller in accordance with the invention for stirring microcarrier beads within a liquid culture suspension contained within the bioreactor.

FIG. 8 depicts a bioreactor (40) which contains a liquid growth medium (50) being stirred with an impeller (10) in accordance with the invention. The impeller (10) is connected to a drive shaft (60) which in turn is coupled to an electric motor (70) via a gear box (75). The dotted lines indicate the upward flow of media generated by the rotation of the impeller blades (30).

Figure 9:
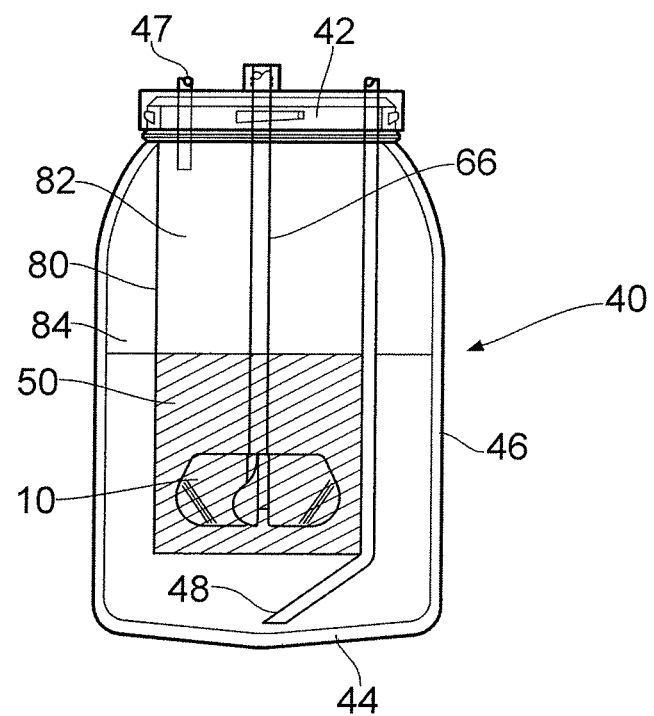
FIG. 9 is a schematic illustration of a cell separator which can be used for separating cells from microcarrier beads.

FIG. 9 illustrates a cell separator (40) which can be used to facilitate cell separation from microcarrier beads. In the simplified embodiment shown, the separator has a head plate (42), with a cylindrical wall (46) connected to a base (44) by attachment means (not shown). A cylindrical sieve (80) or mesh filter, which is closed at one end and attached at its open end to a head plate (42), forms an inner chamber (82) for separating cells from microcarrier beads therein, and an outer chamber (84) for the collection of cells which have been separated from beads through sieve (80). An impeller (10), attached to drive shaft (60) which runs through the head plate (42) and is connected to a suitable drive means (e.g. an electric motor, not shown) is enclosed by the sieve (80) and is positioned within the inner chamber (82). A mixture (50) of cells and microcarrier beads (which have been treated with an enzymic solution or disassociation solution such as trypsin) is fed into the inner chamber (82) via inlet tube (47) by vacuum or positive pressure. The sieve (80) has a first mesh which is composed of pores of a size that permits the flow of cells through to the outer chamber (84) but excludes the passage of microcarriers. The pore sizes are in the range of 50 to 150 µm, typically in the range of 60 to 120 µm, preferably in the range of 70 to 80 µm. The sieve (80) may also be supported by a second mesh which has pores of a size which is larger than that of the first mesh. In operation, cells in the trypsinised mixture (50) are forced through the pores of the sieve (80) by the rotation of the impeller (10), which is turning at speeds of 25 to 50 rpm, leaving the microcarrier beads in the inner chamber (82). Further washing of the trypsinised mixture with suitable buffers ensures that a large proportion of the cell population is washed from the beads. The cells which pass into the outer chamber (84) are collected by pumping them via outlet (48) to a suitable collection vessel (not shown). Cell recovery rates using the cell separator are typically in the order of 88 to 90%.

The bioreactor or the cell separator of the invention can be sterilised by conventional means such as autoclaving, chemical disinfection and gamma-radiation.

A sparger (not shown), positioned below the impeller (10), can also be used to enhance cell/microcarrier bead separation. In a preferred embodiment the sparger is attached to the inlet (47) and comprises a spiral tube having a plurality of holes within. In operation, a trypsinised mixture of beads and cells are forced through these holes into the inner chamber (82) by the application of a suitable positive or negative pressure. The trypsinised mixture is thus subjected to additional mixing and agitation which, together with the dynamic forces exerted by the rotational action of the impeller, increases the efficiency of separation of cell from carrier bead. The cells become detached from the microcarrier beads and are separated from them as they are forced from the inner chamber (82) through the sieve (80) to the outer chamber (84). Collection of cells can be effected via outlet (48) as described above.

It will be understood by the person skilled in the art that cell separation can also be effected using the apparatus described above (and illustrated in FIG. 9) without the use of the impeller. In this instance, the impeller is replaced by the use of a sparger to agitate the cells and microcarrier beads and bring about cell separation. Suitable spargers include those described above.

Comparison of Cell Growth Using a Marine Impeller Versus an Impeller of the Invention ("Custom Impeller") in a BioFlo 110 Bioreactor Using Chinese Hamster Ovary (CHO) DP1 Cells Introduction This experiment was designed to compare cell growth and cell performance in an assay using a standard marine impeller (New Brunswick Scientific, New Jersey, USA, part number M1273-9901) and an impeller according to the invention ("Custom Impeller").

Chinese Hamster Ovary (CHO) DP1 are adherent or anchorage-dependent cells. A vial of cells from ATCC (American Type Culture Collection) were grown in CORNING® CELLSTACK® culture chambers up to a total count of approximately 1×10⁹ (The protocol for using the CORNING® CELLSTACK® culture chambers can be found on the Corning website before transferring to a BioFlo 110 3.5 L bioreactor (New Brunswick Scientific Inc, New Jersey, USA) for seeding on to 20 g of CYTODEX™ 3 beads (GE Healthcare) per flask. This bioreactor was fitted with a spin filter to enable medium changes without removing the seeded microcarriers and was fitted with the custom impeller. After seeding, the culture was grown overnight before removing 50% of the culture to a second BioFlo 110 bioreactor which was fitted with spin filter and a standard marine impeller.

Agitation was 25 rpm for the custom impeller and 80 rpm for the marine impeller. Other parameters were set at pH 7.2, dissolved oxygen 40%, temperature 37° C.

The medium used was standard for this cell type but with selection i.e.

| GLUTAMAX ™ media | 500 ml | Gibco 61965 |
| --- | --- | --- |
| Foetal Calf Serum | 50 ml | PAA A15-151 |
| Penicillin/Streptomycin | 5 ml | Sigma P4333 |
| Non essential Amino Acids | 5 ml | Sigma M7145 |
| Sodium pyruvate | 5 ml | Sigma S8636 |
| GENETICIN ® | 8 ml | Gibco 10131-027 |
| ZEOCIN ™ | 1.25 ml | Invitrogen 45-0003 |

The medium was changed twice a day from T3 (T0=day 1). The medium in both bioreactors was changed by pumping in and out from separated reservoirs Results Cells were seeded as normal in the spinner flasks before being transferred to the bioreactors.

Figure 10:
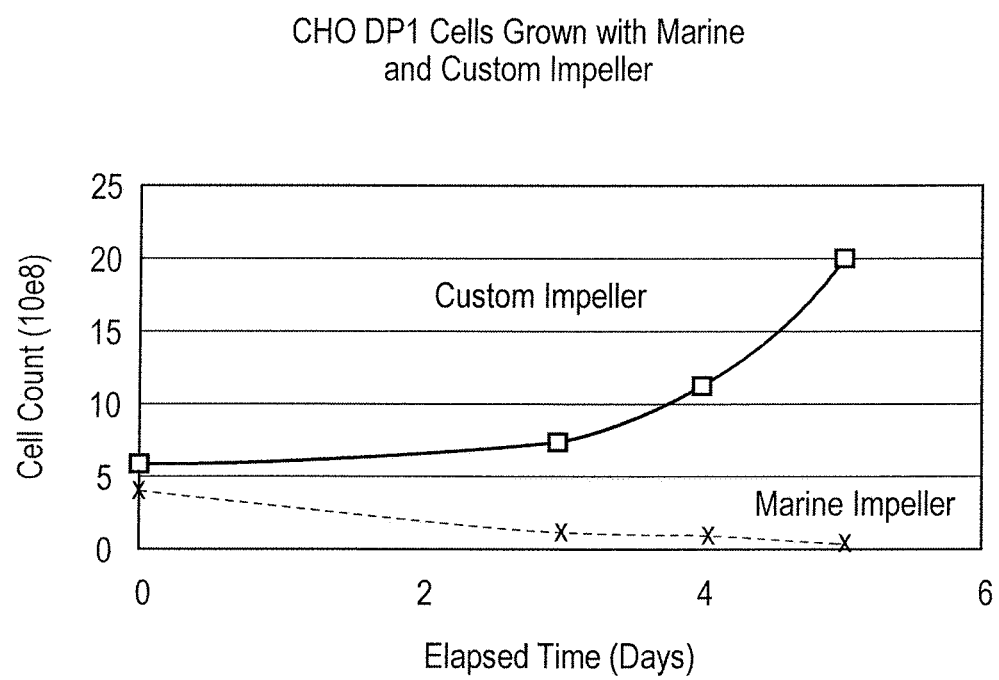
FIG. 10 is a time course showing the growth of Chinese Hamster Ovary (CHO) cells grown in a bioreactor stirred by a prior art impeller (Marine) and an impeller according to the invention (Custom impeller).

Growth Curves for both methods are shown in FIG. 10; the data demonstrate that significantly greater cell growth occurred in the bioreactor stirred by the custom impeller than with the marine impeller.

Whilst the present invention has been described in connection with various embodiments, those skilled in the art will be aware that many different embodiments and variations are possible. All such variations and embodiments are intended to fall within the scope of the present invention as defined by the appended claims.

What is claimed is:

1. An impeller for use in a bioreactor for adherent mammalian cells and/or a cell separator for adherent mammalian cells comprising:
    a hub attachable to a rotatable shaft;
    one or more blades attached to said hub;
    each said blade comprising:
    a first side adjacent to the hub;
    a second side and a third side adjacent to and at right angles to said first side, said second and third sides defining a height therebetween;
    a fourth side opposed to the first side and forming an outer edge of the blade, said outer edge disposed at a length from said hub; and
    a surface having a planar portion and a curved portion;
    wherein said curved portion is angled in the range of 70 to 120° to the plane of said planar portion to form a leading surface relative to the direction of rotation of said impeller,
    wherein the second side is shorter than the third side,
    wherein the impeller is configured to turn the mammalian cells at low shear force to minimize cellular injury,
    wherein the fourth side outer edge includes a generally straight portion merging into said curved portion; and
    said length being greater than said height.

2. The impeller of claim 1, wherein the curved portion is angled in the range of 80 to 100° to the plane of the curved portion.

3. The impeller of claim 1, wherein the curved portion is angled at 90° to the plane of the planar portion (36).

4. The impeller of claim 1, wherein the curved portion constitutes 20 to 40% of the area of said surface.

5. The impeller of claim 1, wherein the curved portion is curved upwards.

6. A method for growing adherent mammalian cells, said method comprising:
    a) adding adherent mammalian cells to growth medium in a bioreactor;
    b) stirring said growth medium with the impeller of claim 1;
    wherein the impeller is rotated at a speed of 10 to 55 rpm.

7. The method of claim 6, wherein said cells are attached to microcarrier beads prior to adding the cells to said growth medium in said bioreactor.

8. The method of claim 6, wherein the growth medium contains microcarrier beads and the cells attach to said beads while the impeller is stirring the growth medium.

9. The method of claim 6, wherein the impeller is rotated at a speed of 15 to 30 rpm.

10. A bioreactor or a cell separator comprising the impeller of claim 1.

11. The bioreactor or cell separator of claim 10, further comprising a head plate, a cylindrical wall, and a base, wherein said cylindrical wall is secured to said head plate and said base.

12. The cell separator of claim 11, further comprising:
    a cylindrical sieve attached to the head plate and enclosing the impeller to form an inner chamber for separating cells from microcarrier beads within and an outer chamber for collecting cells therefrom;
    an inlet for feeding cells and microcarrier beads into the inner chamber; and
    an outlet for collecting cells from the outer chamber;
    wherein the sieve comprises a first mesh having a plurality of pores of a size that permits the flow of cells through to said outer chamber but excludes the passage of microcarrier beads.

13. The cell separator of claim 12, wherein said sieve additionally comprises a second mesh having a plurality of pores of a size greater than that of said pores of said first mesh.

14. The cell separator of claim 12, further comprising a sparger attached to said inlet.

\* \* \* \* \*